United States Patent
Auer et al.

(10) Patent No.: US 9,346,886 B2
(45) Date of Patent: May 24, 2016

(54) HUMANIZED ANTI-CDCP1 ANTIBODIES

(71) Applicant: Roche Glycart AG, Schlieren (CH)

(72) Inventors: Johannes Auer, Schwaigen (DE); Birgit Bossenmaier, Seefeld (DE); Guy Georges, Habach (DE); Alexander Lifke, Penzberg (DE); Ekkehard Moessner, Kreuzlingen (CH); Gerhard Niederfellner, Oberhausen (DE)

(73) Assignee: Roche Glycart AG, Schlieren (CH)

( * ) Notice: Subject to any disclaimer, the term of this patent is extended or adjusted under 35 U.S.C. 154(b) by 188 days.

(21) Appl. No.: 13/721,553

(22) Filed: Dec. 20, 2012

(65) Prior Publication Data

US 2013/0209455 A1 Aug. 15, 2013

Related U.S. Application Data

(62) Division of application No. 12/868,845, filed on Aug. 26, 2010, now Pat. No. 8,394,928.

(30) Foreign Application Priority Data

Aug. 28, 2009 (EP) .................................... 09011046
Feb. 1, 2010 (EP) .................................... 10000972

(51) Int. Cl.
*C07K 16/00* (2006.01)
*C07K 16/30* (2006.01)
*C07K 16/28* (2006.01)

(52) U.S. Cl.
CPC ............. *C07K 16/30* (2013.01); *C07K 16/2896* (2013.01); *C07K 2317/24* (2013.01); *C07K 2317/41* (2013.01); *C07K 2317/56* (2013.01); *C07K 2317/72* (2013.01); *C07K 2317/73* (2013.01); *C07K 2317/732* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,815,540 B1 | 11/2004 | Plückthun et al. | |
| 8,394,928 B2 * | 3/2013 | Auer et al. ................. | 530/387.3 |
| 2004/0053343 A1 | 3/2004 | Buehring et al. | |
| 2007/0031419 A1 | 2/2007 | Domon et al. | |
| 2009/0181033 A1 | 7/2009 | Buehring et al. | |
| 2009/0196873 A1 | 8/2009 | Domon et al. | |
| 2010/0179306 A1 | 7/2010 | Buehring et al. | |

FOREIGN PATENT DOCUMENTS

| | | |
|---|---|---|
| EP | 1396501 | 3/2004 |
| JP | 2007112734 | 5/2007 |
| RU | 2321630 C2 | 4/2010 |
| WO | 02/04508 | 1/2002 |
| WO | 02/04504 | 2/2002 |
| WO | 2004/074481 | 9/2004 |
| WO | 2007/005502 | 1/2007 |
| WO | 2008/133851 | 11/2008 |
| WO | 2005/042102 | 5/2012 |

OTHER PUBLICATIONS

Buhring, Hans-Jorg et al., "CDCP1 Identifies a Broad Spectrum of Normal and Malignant Stem/Progenitor Cell Subsets of Hematopoietic and Nonhematopoietic Origin" Stem Cells (XP-002495598)22:334-343 (2004).
Conze, Tim et al., "CDCP1 is a Novel Marker for Hematopoietic Stem Cells" N.Y. Acad. Sci. (XP-009021998)996:222-226 (2003).
Partial International Search Report dated Oct. 6, 2010, received in International Application No. PCT/EP2010/005245.
European Search Report dated Jan. 4, 2010, received in priority EP Application No. EP 09011046.1.
Hooper, John D. et al., "Subtractive immunization using highly metastatic human tumor cells identifies SIMA135/CDCP1, a 135 kDa cell surface phosphorylated glycoprotein antigen" Oncogene22:1783-1794 (2003).
Nezu, Jun-Ichi et al., "Identification of CDCP1 as a novel molecular target of anti-cancer therapeutic antibody targeting prostate cancer" Abstract (Proceedings of the Annual Meeting of the American Association for Cancer Research; 98th Annual Meeting of the American Association for Cancer Research) 48:153 (Apr. 1, 2007).
Niwa, Rinpei et al. et al., "IgG subclass-independent improvement of antibody-dependent cellular cytotoxicity by fucose removal from Asn297-linked oligosaccharides" J Immunol Methods (XP005197272), 306(1-2):151-160 (Nov. 30, 2005).
Scherl-Mostageer, M. et al., "Identification of a novel gene, CDCP1, overexposed in human colorectal cancer" Oncogene20:4402-4408 (2001).
Shields, Robert L., "Lack of Fucose on Human IgG1 N-Linked Oligosaccharide Improves Binding to Human FcRgammaRIII and Antibody-dependent Cellular Toxicity" J Biol Chem (XP002964542), 277(30):26733-26740 (Jul. 26, 2002).
Siva, Amara C. et al., "Targeting CUB Domain-Containing Protein 1 with a Monoclonal Antibody Inhibits Metastasis in a Prostate Cancer Model" Cancer Research (XP-002559247) 68(10):3759-3766 (May 15, 2008).
Kollmorgen et al., "Antibody mediated CDCP1 degradation as mode of action for cancer targeted therapy" Molecular Oncology 7:1142-1151 ( 2013).
Roitt et al. Immunology "Immunologiya" (Translated by McElroy Translation Company), Fifth Edition edition, Moscow:Mosby International,:110 ( 2000).
Schildbach et al., "Modulation of antibody affinity by non-contact residue" Protein Science 2:206-214 ( 1993).

\* cited by examiner

*Primary Examiner* — Brad Duffy

(57) ABSTRACT

The present invention relates to humanized antibodies against human CDCP1 (anti-CDCP1 antibody), methods for their production, pharmaceutical compositions containing said antibodies, and uses thereof.

2 Claims, 6 Drawing Sheets

Fig. 1

| | |
|---|---|
| mVH-CJB4 | EVQLVESGGDLVKPGGSLKLSCAASGFTFNSYGMSWVRQTPDKRLEWVATISSGGSYTYYPDSVKGRFTISRDNAKNTLYLQMSSLKSEDTAMYYCARHPDYDGVWFAYWGQGTLVTVSA |
| hHC4-H | EVQLVESGGGLVQPGGSLVQPGGSLVQPGGSLRLSCAASGFTFNSYGMSWVRQAPGKGLEWVATISSGGSYTYYPDSVKGRFTISRDNAKNSLYLQMNSLRAEDTAVYYCARHPDYDGVWFAYWGQGTLVTVSS |
| hHC4-c | EVQLVESGGGLVQPGGSLRLSCAASGFTFNSYGMSWVRQAPGKGLEWVATISSGGSYTYYPDSVKGRFTISRDNAKNSLYLQMNSLRAEDTAVYYCARHPDYDGVWFAYWGQGTLVTVSS |
| hHC4-a | EVQLVESGGGLVQPGGSLRLSCAASGFTFNSYGMSWVRQAPGKGLEWVSTISSGGSYTYYPDSVKGRFTISRDNAKNSLYLQMNSLRAEDTAVYYCARHPDYDGVWFAYWGQGTLVTVSS |
| hHC4-d | EVQLLESGGGLVQPGGSLRLSCAASGFTFNSYGMSWVRQAPGKGLEWVSTISSGGSYTYYPDSVKGRFTISRDNSKNTLYLQMNSLRAEDTAVYYCAKHPDYDGVWFAYWGQGTLVTVSS |
| hHC4-04 | EVQLLESGGGLVQPGGSLRLSCAASGFTFNSYGMSWVRQAPGKGLEWVSSISSGGSYTYYPDSVKGRFTISRDNSKNTLYLQMNSLRAEDTAVYYCARHPDYDGVWFAYWGQGTLVTVSS |
| hHC4-K | EVQLVESGGGLVQPGGSLRLSCAASGFTFNSYGMSWVRQAPGKGLEWVSSISSGGSYKYYPDSVKGRFTISRDNAKNSLYLQMNSLRAEDTAVYYCARHPDYDGVWFAYWGQGTLVTVSS |
| hHC4-K2 | EVQLVESGGGLVQPGGSLRLSCAASGFTFNSYGMSWVRQAPGKGLEWVSTISSGGSYKYVDSVKGRFTISRDNAKNSLYLQMNSLRAEDTAVYYCARHPDYDGVWFAYWGQGTLVTVSS |
| hHC4-T | EVQLLESGGGLVQPGGSLRLSCAASGFTFNSYAMSWVRQAPGKGLEWVSAISSGGSYTYYADSVKGRFTISRDNSKNTLYLQMNSLRAEDTAVYYCAKHPDYDGVWFAYWGQGTLVTVSS |
| hHC4-07 | EVQLLESGGGLVQPGGSLRLSCAASGFTFNSYGMSWVRQAPGKGLEWVSTISSGGSYTYYPDSVKGRFTISRDNSKNTLYLQMNSLRAEDTAVYYCAKHPDYDGVWFAYWGQGTLVTVSS |
| hHC4-03 | EVQLLESGGGLVQPGGSLRLSCAASGFTFNSYGMSWVRQAPGKGLEWVSAISSGGSYTYYADSVKGRFTISRDNSKNTLYLQMNSLRAEDTAVYYCAKHPDYDGVWFAYWGQGTLVTVSS |
| hHC4-b | EVQLVESGGGLVKPGGSLRLSCAASGFTFNSYSMNWVRQAPGKGLEWVSSISSGGSYIYYADSVKGRFTISRDNAKNSLYLQMNSLRAEDTAVYYCARHPDYDGVWFAYWGQGTLVTVSS |

Fig. 2

| | |
|---|---|
| mVL-CUB4 | QIVLTQSPAIMSASPGEKVTMTCSVSSSVFYIHWYQQKSGTSPKRWIYDTSKLASGVPARFSGSGSGTSYSLTISSMEAEDAATYYCQQWNSNPPTFGGGTKLEIK |
| hLC4-M | EIVLTQSPATLSLSPGERATMSCGASSSVFYLHWYQQKPGLAPRLWIYDTSKLASGIPDRFSGSGSGTDFTLTISRLEPEDFAVYYCQQWNSNPPTFGGGTKVEIK |
| hLC4-L2 | EIVLTQSPATLSLSPGERATMSCSVSSSVFYLHWYQQKPGQAPRLWIYDTSKLASGIPARFSGSGSGTDFTLTISSLEPEDFAVYYCQQWNSNPPTFGGGTKVEIK |
| hLC4-K | EIVLTQSPATLSLSPGERATLSCRASSSVFYLHWYQQKPGQAPRLWIYDTSKLASGIPARFSGSGSGTDFTLTISSLEPEDFAVYYCQQWNSNPPTFGGGTKVEIK |
| hLC4-L | EIVLTQSPATLSLSPGERATMSCRASSSVFYLHWYQQKPGQAPRLWIYDTSKLASGIPARFSGSGSGTDFTLTISSLEPEDFAVYYCQQWNSNPPTFGGGTKVEIK |
| hLC4-J | EIVMTQSPATLSLSPGERATMSCRASSSVFYLHWYQQKPGQAPRLWIYDTSKLASGIPARFSGSGSGTDFTLTISSLQPEDFAVYYCQQWNSNPPTFGGGTKVEIK |
| hLC4-b | EIVLITQSPATLSLSPGERATLSCSVSSSVFYVHWYQQKPGQAPRLLIYDTSKLASGIPARFSGSGSGTDYTLTISSLEPEDFAVYYCQQWNSNPPTFGGGTKVEIK |
| hLC4-c | EIVMTQSPATLSVSPGERATLSCSVSSSVFYVHWYQQKPGQAPRLLIYDTSKLASGIPARFSGSGSGTEFTLTISSLQSEDFAVYYCQQWNSNPPTFGGGTKVEIK |
| hLC4-a | EIVLTQSPATLSLSPGERATLSCSVSSSVFYVHWYQQKPGQAPRLLIYDTSKLASGIPARFSGSGSGTDFTLTISSLEPEDFAVYYCQQWNSNPPTFGGGTKVEIK |
| hLC4-d | EIVMTQSPATLSVSPGERATLSCSVSSSVFYVHWYQQKPGQAPRLLIYDTSKLASGIPARFSGSGSGTEYTLTISSLQSEDFAVYYCQQWNSNPPTFGGGTKVEIK |
| hLC4-e | DIQMTQSPSSLSASVGDRVTITCSVSSSVFYVHWYQQKPGKAPKLLIYDTSKLASGVPSRFSGSGSGTDFTFTISSLQPEDIATYYCQQWNSNPPTFGGGTKVEIK |
| hLC4-f | DIQMTQSPSSLSASVGDRVTITCSVSSSVFYVHWYQQKPGKAPKLLIYDTSKLASGVPSRFSGSGSGTDYTFTISSLQPEDIATYYCQQWNSNPPTFGGGTKVEIK |
| hLC4-I | EIVMTQSPATLSLSPGERATLSCRASSSVFYLSWYQQKPGQAPRLWIYDTSKLASGIPARFSGSGSGTDFTLTISSLQPEDFAVYYCQQWNSNPPTFGGGTKVEIK |

Fig. 3

| VH=<br>VL= | chHC4 | hHC4-H | hHC4-c | hHC4-a | hHC4-04 | hHC4-d | hHC4-K2 | hHC4-K | hHC4-I | hHC4-07 | hHC4-03 | hHC4-b |
|---|---|---|---|---|---|---|---|---|---|---|---|---|
| chLC4 | 0,99 | 1,12 | 1,00 | 0,87 | 0,71 | 0,60 | 0,81 | 0,37 | 0,36 | 0,34 | 0,25 | 0,00 |
| hLC4-M | 0,87 | 0,56 | 0,71 | 0,80 | 0,82 | 0,80 | 0,28 | 0,04 | 0,19 | 0,15 | 0,14 | 0,00 |
| hLC4-L2 | 0,67 | 0,69 | 0,53 | 0,58 | 0,67 | 0,49 | 0,20 | 0,06 | 0,21 | 0,13 | 0,18 | 0,00 |
| hLC4-K | 0,63 | 0,46 | 0,83 | 0,51 | 0,57 | 0,52 | 0,30 | 0,06 | 0,09 | 0,10 | 0,15 | 0,00 |
| hLC4-L | 0,59 | 0,44 | 0,45 | 0,55 | 0,68 | 0,56 | 0,21 | 0,02 | 0,11 | 0,19 | 0,17 | 0,00 |
| hLC4-J | 0,49 | 0,52 | 0,42 | 0,43 | 0,40 | 0,38 | 0,15 | 0,01 | 0,11 | 0,07 | 0,08 | 0,00 |
| hLC4-b | 0,46 | 0,53 | 0,28 | 0,36 | 0,36 | 0,38 | 0,12 | 0,00 | 0,07 | 0,07 | 0,07 | 0,00 |
| hLC4-c | 0,38 | 0,44 | 0,29 | 0,35 | 0,33 | 0,45 | 0,09 | 0,00 | 0,05 | 0,04 | 0,07 | 0,00 |
| hLC4-a | 0,36 | 0,51 | 0,34 | 0,38 | 0,39 | 0,34 | 0,10 | 0,00 | 0,08 | 0,06 | 0,07 | 0,00 |
| hLC4-d | 0,36 | 0,34 | 0,36 | 0,28 | 0,41 | 0,41 | 0,08 | 0,00 | 0,06 | 0,04 | 0,07 | 0,00 |
| hLC4-e | 0,32 | 0,47 | 0,25 | 0,46 | 0,20 | 0,27 | 0,07 | 0,00 | 0,07 | 0,07 | 0,05 | 0,00 |
| hLC4-f | 0,24 | 0,42 | 0,34 | 0,50 | 0,37 | 0,40 | 0,09 | 0,00 | 0,09 | 0,07 | 0,07 | 0,00 |
| hLC4-I | 0,00 | 0,00 | 0,00 | 0,00 | 0,00 | 0,00 | 0,00 | 0,00 | 0,00 | 0,00 | 0,00 | 0,00 |

Relative binding ratio: 0.40 or higher
Relative binding ratio: below 0.40 and above 0.20
Relative binding ratio: 0.20 or lower

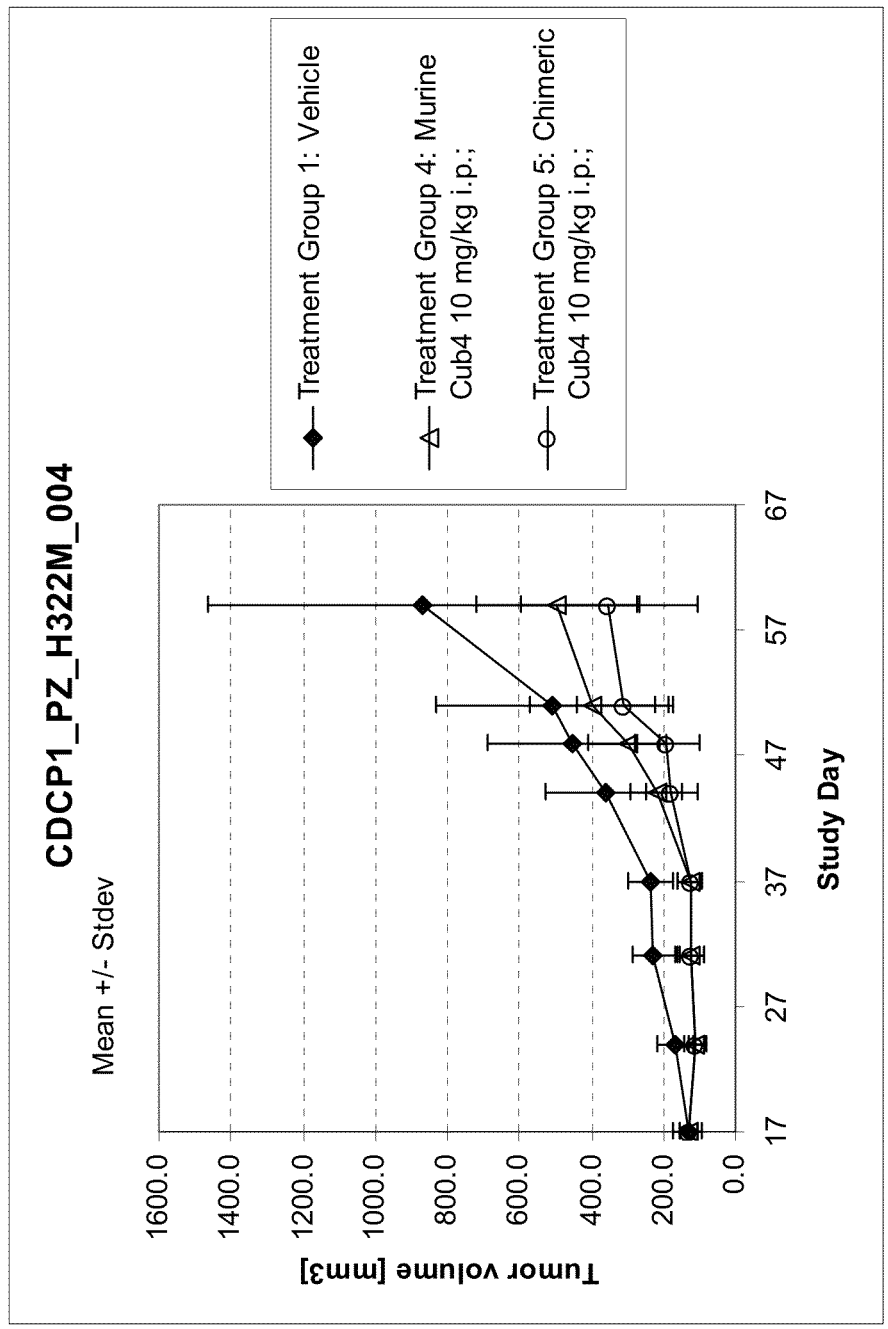

HUMANIZED ANTI-CDCP1 ANTIBODIES

CROSS-REFERENCE TO RELATED APPLICATIONS

This application is a divisional application of U.S. application Ser. No. 12/868,845, filed Aug. 25, 2010, the contents of which are hereby incorporated by reference, and which claims the benefit of the filing date of European patent application 09011046.1, filed Aug. 28, 2009, and European patent application 10000972.9, filed Feb. 1, 2010.

FIELD OF INVENTION

The present invention relates to humanized antibodies against human CDCP1 (anti-CDCP1 antibody), methods for their production, pharmaceutical compositions containing said antibodies, and uses thereof.

BACKGROUND OF THE INVENTION

Human CDCP1 ((CUB domain containing protein 1, B345, CD318, SIMA135, TRASK; SEQ ID NO:29 and variants with mutation R525Q (i.e. replacement of Arginine (R) with Glutamine (Q) at amino acid position 525 of SEQ ID NO:29) and/or mutation G709D (i.e. replacement of Glycine (G) with Aspartic acid (D) at amino acid position 709 of SEQ ID NO:29)) is a transmembrane protein containing three extracellular CUB domains. This protein is found to be overexpressed in breast, colon and lung cancers. Its expression level is correlated with the metastatic ability of carcinoma cells (Uekita, T. et al., Am. J. Pathol. 172 (2008) 1729-1739). It has been shown to be tyrosine phosphorylated in a cancer cell line (WO 2002/004508; Scherl-Mostageer, M., et al., Oncogene 20 (2001) 4402-8; Hooper, J., D., et al., Oncogene 22 (2003) 1783-94; Perry, S., E., et al FEBS Lett. 581 (2007) 1137-42; Brown, T., A., at al J. Biol. Chem. 279 (2004) 14772-14783; Ota, T., et al., Nat. Genet. 36 (2004) 40-45). Alternatively spliced transcript variants encoding distinct isoforms have been reported.

WO 2002/004508 refers to CDCP1 as tumor associated antigen B345. WO 2004/074481 relates to CDCP1 as glycoprotein antigen SIMA135 expressed in metastatic tumor cells. WO 2005/042102 relates to CDCP1 as protein involved in ovarian cancer. WO 2007/005502 relates to methods and compositions for treating diseases targeting CDCP1.

US 2004/0053343 (and Conze, T., et al., Ann. N. Y. Acad. Sci. 996 (2003) 222-6 and Buehring, H. J. et al., Stem Cells 22 (2004) 334-43) relates to CDCP1 antibodies for identifying certain stem cell populations.

SUMMARY OF THE INVENTION

Unless specifically indicated otherwise, all amino acid positions referenced in this specification are numbered according to Kabat.

One aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
    characterized in being humanized and comprising in said VH sequence:
    a Lysine (K) at position 57 instead of Threonine (T), and a Valine (V) at position 60 instead of a Proline (P).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
    characterized in being humanized and comprising in said VL sequence:
    a Leucine (L) at position 33 instead of Valine (V), and a Tryptophan (W) at position 47;

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
    characterized in being humanized,
    and comprising in said VH sequence:
    a Lysine (K) at position 57 instead of Threonine (T), and a Valine (V) at position 60 instead of a Proline (P);
    and comprising in said VL sequence:
    a Leucine (L) at position 33 instead of Valine (V), and a Tryptophan (W) at position 47.

Preferably the humanized antibody according to the invention is characterized in that the heavy chain variable domain (VH) is SEQ ID NO:3.

Preferably the humanized antibody according to the invention is characterized in that the light chain variable domain (VL) is SEQ ID NO: 14, SEQ ID NO: 15, SEQ ID NO: 16, SEQ ID NO: 17, or SEQ ID NO: 18.

Preferably the humanized antibody according to the invention is characterized in that
    the heavy chain variable domain (VH) is SEQ ID NO:3.
    and
    the light chain variable domain (VL) is SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, or SEQ ID NO: 24.

Preferably the humanized antibody according to the invention is characterized in that
    the heavy chain variable domain (VH) is SEQ ID NO:3.
    and
    the light chain variable domain (VL) is SEQ ID NO: 14, SEQ ID NO: 15, SEQ ID NO: 16, SEQ ID NO: 17, or SEQ ID NO: 18.

Preferably the humanized antibody according to the invention is characterized in that said antibody is of human IgG1 subclass.

Preferably the humanized antibody according to the invention is characterized in that said antibody is glycosylated with a sugar chain at Asn297 whereby the amount of fucose within said sugar chain is 65% or lower.

A further embodiment of the invention is a pharmaceutical composition comprising the humanized antibody according to the invention.

A further embodiment of the invention is said pharmaceutical composition comprising the humanized antibody according to the invention for treatment of cancer.

The invention further comprises the humanized antibody according to the invention for treatment of cancer.

The invention further comprises the use the humanized antibody according to the invention for the preparation of a medicament for treatment of cancer.

The invention provides nucleic acid encoding the humanized antibody according to the invention. The invention further provides expression vectors containing nucleic acid according to the invention capable of expressing said nucleic acid in a prokaryotic or eukaryotic host cell, and host cells containing such vectors for the recombinant production of an antibody according to the invention.

The invention further comprises a prokaryotic or eukaryotic host cell comprising a vector according to the invention.

The invention further comprises a method for the production of a recombinant humanized antibody according to the invention, characterized by expressing a nucleic acid according to the invention in a prokaryotic or eukaryotic host cell and recovering said antibody from said cell or the cell culture supernatant. The invention further comprises the antibody obtained by such a recombinant method.

The invention further provides a method for treating a patient suffering from cancer, comprising administering to a patient diagnosed as having such a disease (and therefore being in need of such a therapy) an effective amount of an antibody according to the invention. The antibody is administered preferably in a pharmaceutical composition.

It has now surprisingly found out that the specific humanized versions of the CDCP1 antibody CUB4 according the invention show improved CDCP1-binding properties compared to other humanized versions originating from humanizations known in the prior art. This is due to specific amino acid changes in the CDRH2, and/or in the CDRL1 and in the framework of the light chain. Surprisingly the specific humanized versions of the CDCP1 antibody CUB4 according the invention show improved in vivo tumor growth inhibition compared to the chimeric and mouse CUB4 antibodies.

DESCRIPTION OF THE FIGURES

FIG. 1 VH domain amino acid sequence (CDRH1, CDRH2 and CDRH3 are marked—bold letters) of mouse (mVH-CUB4) antibody and VH domain amino acid sequences of different humanized CUB4 anti-CDCP1 antibodies (specific modifications according to the invention are marked—bold letters)

FIG. 2 VL domain amino acid sequence (CDRL1, CDRL2 and CDRL3 are marked—bold letters) of mouse (mVL-CUB4) antibody and VL domain amino acid sequences of different humanized CUB4 anti-CDCP1 antibodies (specific modifications according to the invention are marked—bold letters)

FIG. 3 Relative binding ratios of different humanized anti-CDCP1 antibodies CUB4. The binding ratios of the combinations of different humanized VH and VL domain relative to chimeric CUB4 ((chHC4=mouse VH and VL with human IgG1 constant region) antibody is shown.

FIGS. 5a and 5b In vivo tumor growth inhibition in human lung cancer H322M xenograft of humanized CUB4 Antibodies No. 69 and No. 135, chimeric CUB4 antibody and mouse CUB4 antibody.

DETAILED DESCRIPTION OF THE INVENTION

Figure 4:
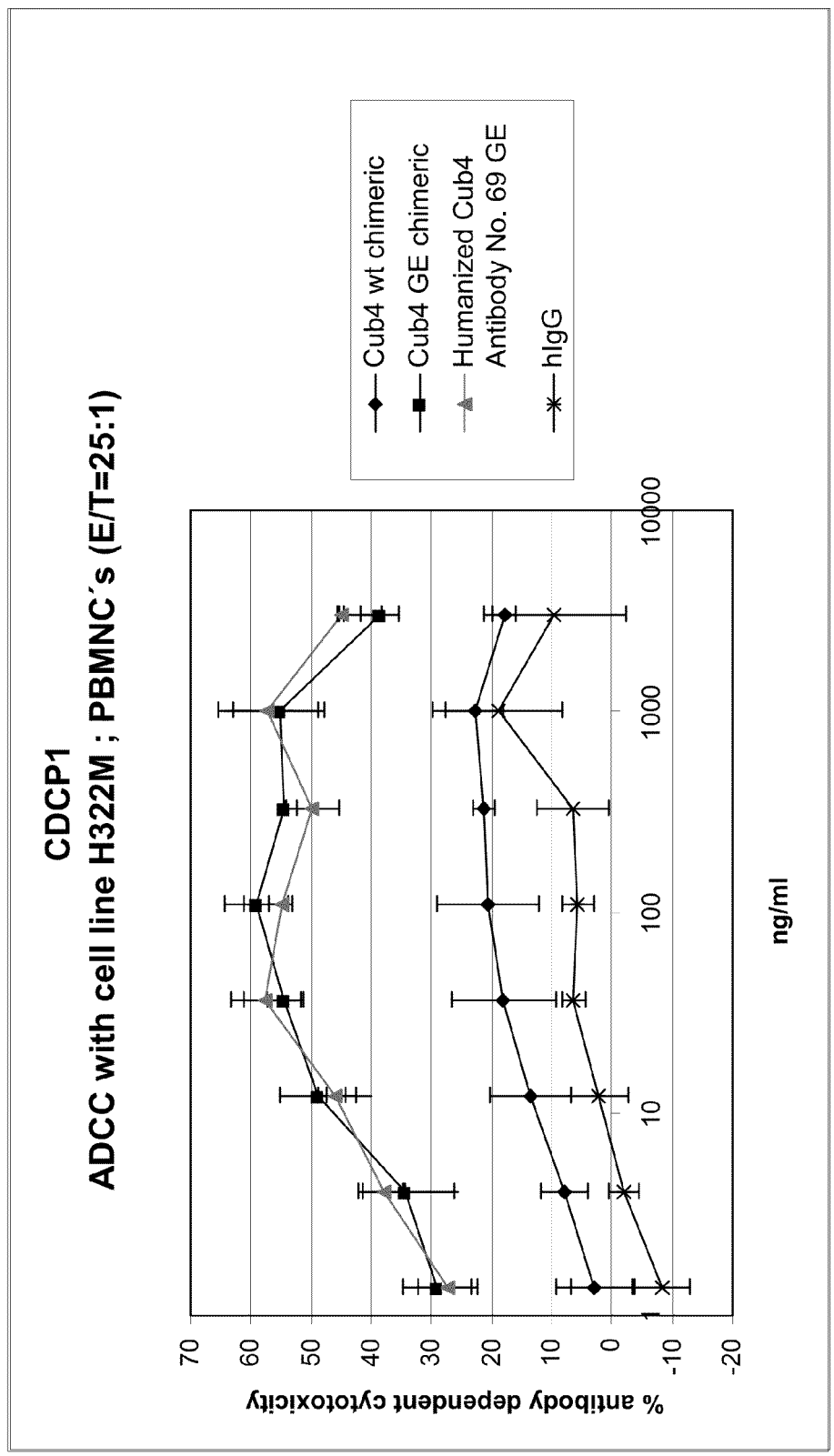
FIG. 4 in vitro ADCC of glycoengineered (GE) humanized CUB4 antibody No. 69 GE with an amount of fucose of 65% or less compared with the ADCC of the chimeric glycoengineered (GE) CUB4 and wildtype (wt=non glycoengineered chimeric CUB4 Antibody and negative human IgG control.

The CUB4 antibody refers to the deposited antibody with the Deposition No. DSM ACC2551 (DSMZ) from DE10242146 (EP 1 396 501, U.S. Pat. No. 7,541,030) with the heavy chain variable domain (VH) of SEQ ID NO:1 and the light chain variable domain (VL) of SEQ ID NO:2. Said CUB4 antibody is specifically binding to human CDCP1.

The term "being humanized" as used herein denotes an antibody, based on the deposited mouse CUB4 antibody with the VH of SEQ ID NO:1 and the VL of SEQ ID NO:2, in which (after chimerization with a human constant region) said VH and VL are humanized by grafting the murine CDRs into the framework region of a human antibody (see e.g. Riechmann, L., et al., Nature 332 (1988) 323-327; and Neuberger, M., S., et al., Nature 314 (1985) 268-270; Queen, C., et al., Proc. Natl. Acad. Sci. USA 86 (1989) 10029-10033; U.S. Pat. No. 5,530,101; U.S. Pat. No. 5,585,089; U.S. Pat. No. 5,693,761; WO 90/07861; and U.S. Pat. No. 5,225,539). The heavy and light chain variable framework regions can be derived from the same or different human antibody sequences. The human antibody sequences can be the sequences of naturally occurring human antibodies. Human heavy and light chain variable framework regions are listed e.g. in Lefranc, M. P., Current Protocols in Immunology (2000)—Appendix 1P A.1P.1-A.1P.37 and are accessible via IMGT, the international ImMunoGeneTics information System® (http://imgt.cines.fr) or via http://vbase.mrc-cpe.ca-m.ac.uk.

The humanized antibodies according to the invention have in addition
   a) specific mutations in the CDRH2 of the VH (mutations T57K and P60V). and/or
   b) specific mutations in CDRL1 of the VL (mutation V33L) and in the framework region of VL (backmutation from human VL framework amino acid to mouse amino acid W at position 47).

Such mutations in the humanized CUB antibodies surprisingly lead to improved binding properties (compared to humanized CUB4 antibodies without such modifications). Furthermore such modifications in the CDRs and/or the framework resulted in the humanized antibodies according to the invention with improved in vivo tumor growth inhibition (compared to the chimeric and mouse parent antibodies).

One aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
   characterized in being humanized and comprising in said VH sequence:
   a Lysine (K) at position 57 instead of Threonine (T) (in the CDRH2), and a Valine (V) at position 60 instead of a Proline (P) (in the CDRH2) (all positions being numbered according to Kabat). This means that SEQ ID NO:1 comprises the mutations T57K and P60V in the CDRH2 of VH.

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
   characterized in being humanized and comprising in said VL sequence:
   a Leucine (L) at position 33 instead of Valine (V) (in the CDRL1), and a Tryptophan (W) at position 47 (instead of an amino acid from a human VL framework region) (all positions being numbered according to Kabat). This means that SEQ ID NO:2 comprise the mutation V33L in the CDRL1 and a backmutation from human to mouse amino acid W at position 47 in the framework region VL.

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
   characterized in being humanized,
   and comprising in said VH sequence:

a Lysine (K) at position 57 instead of Threonine (T) (in the CDRH2), and a Valine (V) at position 60 instead of a Proline (P) (in the CDRH2); and comprising in said VL sequence:

a Leucine (L) at position 33 instead of Valine (V) and a Tryptophan (W) at position 47 (all positions being numbered according to Kabat). This means that SEQ ID NO:1 comprises the mutations T57K and P60V in the CDRH2 of VH and that SEQ ID NO:2 comprises the mutation V33L in the CDRL1 of VL and a backmutation from human to mouse amino acid W at position 47 in the framework region of VL.

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized and comprising in said VL sequence:
a Leucine (L) at position 33 instead of Valine (V) (in the CDRL1), and a Tryptophan (W) at position 47 (instead of an amino acid from a human VL framework region);
and being further characterized in (further) comprising in said VL sequence:
a Methionine (M) at position 21 (instead of an amino acid from a human VL framework region) (all positions being numbered according to Kabat).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized,
and comprising in said VH sequence:
a Lysine (K) at position 57 instead of Threonine (T) (in the CDRH2), and a Valine (V) at position 60 instead of a Proline (P) (in the CDRH2);
and comprising in said VL sequence:
a Leucine (L) at position 33 instead of Valine (V) and a Tryptophan (W) at position 47 (instead of an amino acid from a human VL framework region);
and being further characterized in (further) comprising in said VL sequence:
a Methionine (M) at position 21 (instead of an amino acid from a human VL framework region) (all positions being numbered according to Kabat).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized and comprising in said VL sequence:
a Leucine (L) at position 33 instead of Valine (V) (in the CDRL1), and a Tryptophan (W) at position 47 (instead of an amino acid from a human VL framework region);
and being further characterized in (further) comprising in said VL sequence:
a Methionine (M) at position 21 (instead of an amino acid from a human VL framework region); a Glycine (G) or a Arginine (R) at position 24 instead of a Serine (S) (in the CDRL1), and Alanine (A) at position 25 instead of a Valine (V) (in the CDRL1) (all positions being numbered according to Kabat).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized,
and comprising in said VH sequence:
a Lysine (K) at position 57 instead of Threonine (T) (in the CDRH2), and a Valine (V) at position 60 instead of a Proline (P) (in the CDRH2);
and comprising in said VL sequence:
a Leucine (L) at position 33 instead of Valine (V) and a Tryptophan (W) at position 47 (instead of an amino acid from a human VL framework region);
and being further characterized in (further) comprising in said VL sequence:
a Methionine (M) at position 21 (instead of an amino acid from a human VL framework region), a Glycine (G) or a Arginine (R) at position 24 instead of a Serine (S) (in the CDRL1), and Alanine (A) at position 25 instead of a Valine (V) (in the CDRL1) (all positions being numbered according to Kabat).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized and comprising in said VL sequence:
a Leucine (L) at position 33 instead of Valine (V) (in the CDRL1), and a Tryptophan (W) at position 47 (instead of an amino acid from a human VL framework region);
and being further characterized in (further) comprising in said VL sequence:
a Arginine (R) at position 24 instead of a Serine (S) (in the CDRL1), and Alanine (A) at position 25 instead of a Valine (V) (in the CDRL1) (all positions being numbered according to Kabat).

Another aspect of the present invention is an antibody specifically binding to human CDCP1 comprising a variable heavy chain domain (VH) of SEQ ID NO:1 and a variable light chain domain (VL) of SEQ ID NO:2 of CUB4 antibody (Deposition No. DSM ACC2551),
characterized in being humanized,
and comprising in said VH sequence:
a Lysine (K) at position 57 instead of Threonine (T) (in the CDRH2), and a Valine (V) at position 60 instead of a Proline (P) (in the CDRH2);
and comprising in said VL sequence:
a Leucine (L) at position 33 instead of Valine (V) and a Tryptophan (W) at position 47 (instead of an amino acid from a human VL framework region;
and being further characterized in (further) comprising in said VL sequence:
a Arginine (R) at position 24 instead of a Serine (S) (in the CDRL1), and Alanine (A) at position 25 instead of a Valine (V) (in the CDRL1) (all positions being numbered according to Kabat).

In one embodiment of the invention the humanized antibody according to the invention is characterized in that
the heavy chain variable domain (VH) is SEQ ID NO:3.

In another embodiment of the invention the humanized antibody according to the invention is characterized in that
the light chain variable domain (VL) is SEQ ID NO: 14, SEQ ID NO: 15, SEQ ID NO: 16, SEQ ID NO: 17, or SEQ ID NO: 18.

In another embodiment of the invention the humanized antibody according to the invention is characterized in that
the heavy chain variable domain (VH) is SEQ ID NO:3.
and
the light chain variable domain (VL) is SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, or SEQ ID NO: 24.

In another embodiment of the invention the humanized antibody according to the invention is characterized in that
the heavy chain variable domain (VH) is SEQ ID NO:3. and
the light chain variable domain (VL) is SEQ ID NO: 14, SEQ ID NO: 15, SEQ ID NO: 16, SEQ ID NO: 17, or SEQ ID NO: 18.

In another embodiment of the invention the humanized antibody according to the invention is characterized in that
the heavy chain variable domain (VH) is SEQ ID NO:3. and
the light chain variable domain (VL) is SEQ ID NO: 14.

In another embodiment of the invention the humanized antibody according to the invention is characterized in that
the heavy chain variable domain (VH) is SEQ ID NO:3. and
the light chain variable domain (VL) is SEQ ID NO: 15.

In another embodiment of the invention the humanized antibody according to the invention is characterized in that
the heavy chain variable domain (VH) is SEQ ID NO:3. and
the light chain variable domain (VL) is SEQ ID NO: 16.

In another embodiment of the invention the humanized antibody according to the invention is characterized in that
the heavy chain variable domain (VH) is SEQ ID NO:3. and
the light chain variable domain (VL) is SEQ ID NO: 17.

In another embodiment of the invention the humanized antibody according to the invention is characterized in that
the heavy chain variable domain (VH) is SEQ ID NO:3. and
the light chain variable domain (VL) is SEQ ID NO: 18.

In another embodiment of the invention the humanized antibody according to the invention is characterized in that
the heavy chain variable domain (VH) is SEQ ID NO:3. and
the light chain variable domain (VL) is SEQ ID NO: 23.

In another embodiment of the invention the humanized antibody according to the invention is characterized in that said antibody is of human IgG1 subclass.

In another embodiment of the invention the humanized antibody according to the invention is characterized in that said antibody is glycosylated with a sugar chain at Asn297 whereby the amount of fucose within said sugar chain is 65% or lower.

Preferred embodiments of the humanized antibody according to the invention are characterized by one of the following combinations of a humanized variable heavy chain domain VH and a humanized variable light chain domain VL, as shown in Table 1 (see the following Example Nos.).

TABLE 1

Preferred combinations of a humanized variable heavy chain domain VH and a humanized variable light chain domain VL.

| Humanized CUB4 Antibody Example No | VL (SEQ ID NO:) | VL (SEQ ID NO:) |
|---|---|---|
| 80 | hHC4-H (SEQ ID NO: 3) | hLC-M (SEQ ID NO: 14) |
| 69 | hHC4-H (SEQ ID NO: 3) | hLC-L2 (SEQ ID NO: 15) |
| 47 | hHC4-H (SEQ ID NO: 3) | hLC-K (SEQ ID NO: 16) |
| 58 | hHC4-H (SEQ ID NO: 3) | hLC-L (SEQ ID NO: 17) |
| 36 | hHC4-H (SEQ ID NO: 3) | hLC-J (SEQ ID NO: 18) |
| 102 | hHC4-H (SEQ ID NO: 3) | hLC-b (SEQ ID NO: 19) |
| 113 | hHC4-H (SEQ ID NO: 3) | hLC-c (SEQ ID NO: 20) |

TABLE 1-continued

Preferred combinations of a humanized variable heavy chain domain VH and a humanized variable light chain domain VL.

| Humanized CUB4 Antibody Example No | VL (SEQ ID NO:) | VL (SEQ ID NO:) |
|---|---|---|
| 91 | hHC4-H (SEQ ID NO: 3) | hLC-a (SEQ ID NO: 21) |
| 124 | hHC4-H (SEQ ID NO: 3) | hLC-d (SEQ ID NO: 22) |
| 135 | hHC4-H (SEQ ID NO: 3) | hLC-e (SEQ ID NO: 23) |
| 146 | hHC4-H (SEQ ID NO: 3) | hLC-f (SEQ ID NO: 24) |

Further preferred embodiments of the humanized antibody according to the invention are characterized by one of the following combinations of a humanized variable heavy chain domain VH and a humanized variable light chain domain VL, as shown in Table 2. Such combinations comprising a human the following Example No., as shown in Table 2.

TABLE 2

Further preferred combinations of a humanized variable heavy chain domain VH and a humanized variable light chain domain VL.

| Humanized CUB4 Antibody Example No | VL (SEQ ID NO:) | VL (SEQ ID NO:) |
|---|---|---|
| 80 | hHC4-H (SEQ ID NO: 3) | hLC-M (SEQ ID NO: 14) |
| 69 | hHC4-H (SEQ ID NO: 3) | hLC-L2 (SEQ ID NO: 15) |
| 47 | hHC4-H (SEQ ID NO: 3) | hLC-K (SEQ ID NO: 16) |
| 58 | hHC4-H (SEQ ID NO: 3) | hLC-L (SEQ ID NO: 17) |
| 36 | hHC4-H (SEQ ID NO: 3) | hLC-J (SEQ ID NO: 18) |

The term "Kabat numbering" or "numbering according to Kabat" or "EU index" unless otherwise stated, is defined as the numbering of the residues in, e.g., an IgG antibody using the EU index as in Kabat et al. (Sequences of Proteins of Immunological Interest, 5th ed., Public Health Service, National Institutes of Health, Bethesda, Md. (1991)).

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such mouse/human chimeric antibodies are the product of expressed immunoglobulin genes comprising DNA segments encoding mouse immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art (see, e.g., Morrison, S., L., et al., Proc. Natl. Acad Sci. USA 81 (1984) 6851-6855; U.S. Pat. No. 5,202,238 and U.S. Pat. No. 5,204,244).

Human CDCP1 ((CUB domain containing protein 1, B345, CD318, SIMA135, TRASK; SEQ ID NO:29 and variants with mutation R525Q (i.e. replacement of Arginine (R) with Glutamine (Q) at amino acid position 525 of SEQ ID NO:29) and/or mutation G709D (i.e. replacement of Glycine (G) with Aspartic acid (D) at amino acid position 709 of SEQ ID NO:29)) is a transmembrane protein containing three extracellular CUB domains. This protein is found to be overexpressed in breast, colon and lung cancers (Uekita, T. et al., Am. J. Pathol. 172 (2008) 1729-1739). Its expression level is correlated with the metastatic ability of carcinoma cells. It has been shown to be tyrosine phosphorylated in a cancer cell line (WO 2002/004508; Scherl-Mostageer, M., et al., Oncogene 20 (2001) 4402-8; Hooper, J., D., et al., Oncogene 22 (2003) 1783-94; Perry, S. E., et al., FEBS Lett. 581 (2007) 1137-42; Brown, T. A., et al., J. Biol. Chem. 279 (2004) 14772-14783; Ota, T., et al., Nat. Genet. 36 (2004) 40-45). Alternatively spliced transcript variants encoding distinct isoforms have been reported.

As used herein, "specifically binding to human CDCP1" refers to an antibody specifically binding to the human CDCP1 antigen. The binding affinity is of KD-value of $1.0 \times 10^{-8}$ mol/l or lower (e.g. $1.0 \times 10^{-8}$ mol/l to $1.0 \times 10^{-13}$ mol/l), preferably of a KD-value of $5.0 \times 10^{-9}$ mol/l or lower (e.g. $5.0 \times 10^{-9}$ mol/l to $1.0 \times 10^{-13}$ mol/l). The binding affinity is determined with a standard binding assay, such as surface plasmon resonance technique (Biacore®).

The term "epitope" denotes a protein determinant of human CDCP1 capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

"Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". The term "antigen-binding portion" of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The term "CDRH1" denotes the CDR1 region of the heavy chain variable region calculated according to Kabat. CDRH2, CDRH3, CDRL1, CDRL2 and CDRL3 mean the respective regions from the heavy (H) or light (L) chain. The extent of CDR and framework regions (FRs) is determined by comparison to a compiled database of amino acid sequences in which those regions have been defined according to variability among the sequences according to Kabat, et al., supra.

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The antibody according to the invention is characterized in that the constant region is of human origin, and is preferably of human IgG1 subclass. The constant region includes the heavy chain and light chain constant region of an antibody. The heavy chain constant region comprises in N-terminal to C-terminal direction an antibody constant heavy chain domain 1 (CH1), an antibody hinge region (HR), an antibody heavy chain constant domain 2 (CH2), and an antibody heavy chain constant domain 3 (CH3), and optionally, in case of an antibody of the subclass IgE, an antibody heavy chain constant domain 4 (CH4). The light chain constant region comprises an antibody light chain constant domain (CL). The antibody light chain constant domain (CL) can be κ (kappa) or λ (lambda). Such constant chains are well known in the state of the art and e.g. described by Kabat, E. A., (see e.g. Johnson, G. and Wu, T., T., Nucleic Acids Res. 28 (2000) 214-218). For example, a useful human heavy chain constant region of IgG1 subclass comprises an amino acid sequence of SEQ ID NO: 26. For example, a useful human light chain constant region comprises an amino acid sequence of a kappa-light chain constant region of SEQ ID NO: 27; another useful human light chain constant region comprises an amino acid sequence of a lambda-light chain constant region of SEQ ID NO: 28.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively.

The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743; Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virology 75 (2001) 12161-12168; Morgan, A., et al., Immunology 86 (1995) 319-324; EP 0307434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

The antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Mostly preferred are the human heavy chain constant regions of human IgG1 subclass with SEQ ID NO: 26 or 31, of human IgG1 subclass with mutations L234A and L235A, of human IgG4 subclass with SEQ ID NO: 32, or of human IgG4 subclass with mutation S228P.

The term "antibody-dependent cellular cytotoxicity (ADCC)" refers to lysis of human target cells by an antibody according to the invention in the presence of effector cells. ADCC is measured preferably by the treatment of a preparation of CDCP1 expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M., R., et al., Glycobiology 5 (1995) 813-822; Jefferis, R., et al., Immunol. Rev. 163 (1998) 59-76; Wright, A., and Morrison, S., L., Trends Biotechnol. 15 (1997) 26-32). Umana, P., et al., Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies are reported e.g. in WO 2005/044859, WO 2004/065540, WO2007/031875, Umana, P., et al., Nature Biotechnol. 17 (1999) 176-180, WO 99/154342, WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835 and WO 2000/061739 or e.g. in Niwa, R., et al., J. Immunol. Methods 306 (2005) 151-160; Shinkawa, T., et al., J. Biol. Chem. 278 (2003) 3466-3473; WO 03/055993 and US 2005/0249722.

Therefore in one embodiment of the invention, the antibody according to the invention is glycosylated (if it comprises an Fc part of IgG1 or IgG3 subclass) with a sugar chain at Asn297 whereby the amount of fucose within said sugar chain is 65% or lower (Numbering according to Kabat). In another embodiment is the amount of fucose within said sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antibody according to the invention the IgG subclass is of human IgG1 subclass, or of IgG3 subclass. In a further embodiment the amount of N-glycolylneuraminic acid (NGNA) is 1% or less and/or the amount of N-terminal alpha-1,3-galactose is 1% or less within said sugar chain. The sugar chains show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., supra, and by Brueggemann, M., et al., J. Exp. Med. 166 (1987) 1351-1361;

Love, T. W., et al., Methods Enzymol. 178 (1989) 515-527. These structures are designated as G0, G1 ($\alpha$-1,6- or $\alpha$-1,3-), or G2 glycan residues, depending from the amount of terminal Gal residues (Raju, T., S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value (see e.g. WO 2008/077546). The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis).

Recombinant production of antibodies is well-known in the state of the art and described, for example, in the review articles of Makrides, S., C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al. (ed.), Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E. J., and Christensen, K., in Cytotechnology 30 (1999) 71-83 and by Schlaeger, E. J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F., L., and van der Eb, Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N., et al., PNAS 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

Furthermore such specific humanized versions of the CDCP1 antibody CUB4 have turned out to be especially useful for the treatment of cancer compared with e.g. other anti-CDCP1 antibodies Therefore one aspect of the invention is said pharmaceutical composition for the treatment of cancer.

Another aspect of the invention is the humanized antibody according to the invention for the treatment of cancer.

Another aspect of the invention is the use of the humanized antibody according to the invention for the manufacture of a medicament for the treatment of cancer.

Another aspect of the invention is a method of treatment of a patient suffering from cancer by administering the humanized antibody according to the invention to said patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, ovarian cancer, cervical cancer, lung cancer or prostate cancer and more preferably lung cancer. Preferably such cancers are further characterized by CDCP1 expression or overexpression, more preferably by CDCP1 overexpression These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE AMINO ACID SEQUENCES OF THE SEQUENCE LISTING

SEQ ID NO:1 heavy chain variable domain VH of CUB4 (Deposition No. DSM ACC2551)
SEQ ID NO:2 light chain variable domain VL of CUB4 (Deposition No. DSM ACC2551)
SEQ ID NO:3 hHC4-H-humanized VH of CUB4
SEQ ID NO:4 hHC4-c-humanized VH of CUB4
SEQ ID NO:5 hHC4-a-humanized VH of CUB4
SEQ ID NO:6 hHC4-d-humanized VH of CUB4
SEQ ID NO:7 hHC4-04-humanized VH of CUB4
SEQ ID NO:8 hHC4-K-humanized VH of CUB4
SEQ ID NO:9 hHC4-K2-humanized VH of CUB4
SEQ ID NO:10 hHC4-I-humanized VH of CUB4
SEQ ID NO:11 hHC4-07-humanized VH of CUB4
SEQ ID NO:12 hHC4-03-humanized VH of CUB4
SEQ ID NO:13 hHC4-b-humanized VH of CUB4
SEQ ID NO:14 hLC4-M-humanized VL of CUB4
SEQ ID NO:15 hLC4-L2-humanized VL of CUB4
SEQ ID NO:16 hLC4-K-humanized VL of CUB4
SEQ ID NO:17 hLC4-L-humanized VL of CUB4
SEQ ID NO:18 hLC4-J-humanized VL of CUB4
SEQ ID NO:19 hLC4-b-humanized VL of CUB4
SEQ ID NO:20 hLC4-c-humanized VL of CUB4
SEQ ID NO:21 hLC4-a-humanized VL of CUB4
SEQ ID NO:22 hLC4-d-humanized VL of CUB4
SEQ ID NO:23 hLC4-e-humanized VL of CUB4
SEQ ID NO:24 hLC4-f-humanized VL of CUB4
SEQ ID NO:25 hLC4-I-humanized VL of CUB4
SEQ ID NO:26 IgG1 constant heavy chain region from human origin (Caucasian Allotype)
SEQ ID NO:27 kappa constant light chain region from human origin
SEQ ID NO:28 lambda constant light chain region from human origin
SEQ ID NO:29 human CDCP1
SEQ ID NO:30 extracellular-domain-(ECD)-comprising fragment of human CDCP1
SEQ ID NO:31 IgG1 constant heavy chain region from human origin (Afroamerican Allotype)
SEQ ID NO:32 IgG4 constant heavy chain region from human origin

EXAMPLE 1

Antigene Specific ELISA

Soluble CDCP1 extracellular domain (CDCP1-ECD) (SEQ ID NO:30) fused to Streptavidin Binding Protein (SBP) was captured on a sreptavidine plate. To define optimal binding of the antibody to SBP-CDCP1-ECD, 384-well polystyrene plates (NUNC, streptavidin-coated) delivered by Micro-Coat, Bernried, Germany (ID-No. 1734776-001) have been coated with pure and stepwise diluted HEK293 supernatant (in BSA/IMDM buffer:100 mg/ml BSA Fraction V, Roche 10735078001, dissolved in Iscove's Modified Dulbeccos Medium). Using a calibration curve of mouse CUB4 antibodies the optimal dilution factor of the HEK293 supernatant in relation to the streptavidin binding capacity of the microtiter plate was identified. For the standard coating, SBP-CDCP1-ECD containing HEK293 supernatant was diluted (between 1:15 and 1:40) and incubated overnight at 2-8° C. (25 µl per well). Intensive washing of the microtiter plate is necessary to remove remaining unbound SBP-CDCP1-ECD.

Humanized CUB4 antibodies and/or reference antibody (chimeric (chHC4) CUB4 antibody comprising human constant region and mouse VH and VL of SEQ ID NO:1 and 2) were tested either undiluted or using a 12-step-dilution. 12.5 µl per well of each sample was incubated for 90 min at room temperature. After intensive washing using PBS-T (0.1% Tween 20 in PBS) 25 µl of either goat anti-human IgG antibodies coupled with HRP (Jackson ImmunoResearch, Code No: 109-036-098, dilution 1:10000) for human antibodies were added and incubated for 1 hour. After intensive washing the binding of the antibodies was detected with ABTS tablets (Roche Diagnostics GmbH, Cat. No.: 1112422). Absorbance at 405 nm/492 nm was measured using a standard photometer.

In FIG. 3 the binding ratios of the different combinations of humanized VH and VL relative to chimeric (chHC4) CUB4 antibody is shown. The results show that the specific modified humanized antibodies with
  a) specific mutations in the CDRH2 of the VH (mutations T57K and P60V). (see VH domain: hHC4-H (SEQ ID NO: 3),
  and/or
  b) specific mutations in CDRL1 of the VL (mutation V33L) and a mutation from human to mouse amino acid W at position 47 in the VL framework region; (see VL domains: hLC4-M (SEQ ID NO: 14), hLC4-L2 (SEQ ID NO: 15), hLC4-K (SEQ ID NO: 16), hLC4-L (SEQ ID NO: 17), hLC4-J (SEQ ID NO: 18))
surprisingly lead to clearly improved binding properties compared to humanized CUB4 antibodies without such specific modifications.

EXAMPLE 2

Characterization of the Binding of Anti-CDCP1 Antibodies to a Extracellular-Domain-(ECD)-Comprising Fragment of Human CDCP1 of SEQ ID NO.: 30 (Comprising the Extracellular Domain ECD of Human CDCP1)

For affinity measurements, 30 µg/ml anti mouse Fcγ antibodies (from goat, Jackson Immuno Research JIR115-005-071) were coupled to the surface of a CM-5 sensor chip by standard amine-coupling and blocking chemistry on a SPR instrument (Biacore T100). After conjugation, different anti-CDCP1 antibodies were injected at 25° C. at a flow rate of 5 µL/min, followed by a dilution series (0 nM to 1000 nM) of CDCP1 ECD at 30 µL/min. As running buffer for the binding experiment PBS/0.1% BSA was used. The chip was then regenerated with a 60 s pulse of 10 mM glycine-HCl, pH 2.0 solution.

Calculation of thermodynamic parameters ($K_D$, binding constant) and kinetic parameters ($k_{on}$ rate, $k_{off}$ rate) were calculated using a Langmuir 1:1 binding model.

TABLE 3

Exemplary binding parameters of humanized antibodies according to the invention

| Humanized Anti-CDCP1 antibody | $k_a$ [1/Ms] | $k_d$ [1/s] | $t_{1/2}$ diss. [min] | $K_D$ [nM] |
|---|---|---|---|---|
| 47 | 2.0E+05 | 7.5E−04 | 15.4 | 3.77 |
| 69 | 2.1E+05 | 5.2E−04 | 22.1 | 2.55 |
| 80 | 2.5E+05 | 8.8E−04 | 13.1 | 3.53 |
| 91 | 1.8E+05 | 1.0E−03 | 11.2 | 5.60 |
| 102 | 1.9E+05 | 1.1E−03 | 11.0 | 5.40 |
| 135 | 1.4E+05 | 1.1E−03 | 10.3 | 8.30 |

EXAMPLE 3

Preparation of Glycoengineered Humanized CUB4 Antibody (Humanized CUB4 Antibody GE)

The full antibody heavy and light chain DNA sequences corresponding to the amino acid sequences SEQ ID NO:3 and SEQ ID NO:15 (Antibody 69) were subcloned into mammalian expression vectors (one for the light chain and one for the heavy chain) under the control of the MPSV promoter and upstream of a synthetic polyA site, each vector carrying an EBV OriP sequence.

Antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of unmodified antibody, the cells were transfected only with antibody heavy and light chain expression vectors in a 1:1 ratio. For the production of the glycoengineered antibody, the cells were co-transfected with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively. Cells were grown as adherent monolayer cultures in T flasks using DMEM culture medium supplemented with 10% FCS, and were transfected when they were between 50 and 80% confluent. For the transfection of a T150 flask, 15 million cells were seeded 24 hours before transfection in 25 ml DMEM culture medium supplemented with FCS (at 10% V/V final), and cells were placed at 37° C. in an incubator with a 5% CO2 atmosphere overnight. For each T150 flask to be transfected, a solution of DNA, CaCl2 and water was prepared by mixing 94 µg total plasmid vector DNA divided equally between the light and heavy chain expression vectors, water to a final volume of 469 µl and 469 µl of a 1M CaCl2 solution. To this solution, 938 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with 10 ml of DMEM supplemented with 2% FCS, and added to the T150 in place of the existing medium. Then additional 13 ml of transfection medium were added. The cells were incubated at 37° C., 5% CO2 for about 17 to 20 hours, then medium was replaced with 25 ml DMEM, 10% FCS. The conditioned culture medium was harvested 7 days post-transfection by centrifugation for 15 min at 210×g, the solution was sterile filtered (0.22 µm filter) and sodium azide in a final concentration of 0.01% w/v was added, and kept at 4° C.

The secreted antibody glycoengineered humanized CUB4 Antibodies No. 69 (humanized CUB4 Antibodies No. 69 GE) was purified by Protein A affinity chromatography, followed by cation exchange chromatography and a final size exclusion chromatographic step on a Superdex 200 column (Amersham Pharmacia) exchanging the buffer to 25 mM potassium phosphate, 125 mM sodium chloride, 100 mM glycine solution of pH 6.7 and collecting the pure monomeric IgG1 antibodies. Antibody concentration was estimated using a spectrophotometer from the absorbance at 280 nm. The oligosaccharides attached to the Fc region of the antibodies were analysed by MALDI/TOF-MS (as described in e.g. WO 2008/077546). Oligosaccharides were enzymatically released from the antibodies by PNGaseF digestion, with the antibodies being either immobilized on a PVDF membrane or in solution. The resulting digest solution containing the released oligosaccharides either prepared directly for MALDI/TOF-MS analysis or was further digested with EndoH glycosidase prior to sample preparation for MALDI/TOF-MS analysis.

In a further experiment the glycoengineered humanized CUB4 Antibodies (humanized CUB4 Antibody GE) Antibody 69 and 135 were prepared by co-transfection with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively in CHO cells instead of HEK293-EBNA cells. The analyzed amount of fucose within the sugar chain at Asn297 was between 50-10%.

EXAMPLE 4

In Vitro ADCC of Humanized CUB4 Antibodies

The target cells PC-3 (DSMZ #ACC 465, prostatic adenocarcinoma, cultivation in Ham's F12 Nutrient Mixture+2 mM L-alanyl-L-Glutamine+10% FCS) and H322M (non small cell lung carcinoma, cultivation in RPMI1640+2 mM L-alanyl-L-Glutamine+10% FCS) were collected with trypsin/EDTA (Gibco #25300-054) in exponential growth phase. After a washing step and checking cell number and viability the aliquot needed was labeled for 30 min at 37° C. in the cell incubator with calcein (Invitrogen #C3100MP; 1 vial was resuspended in 50 µl DMSO for 5 Mio cells in 5 ml medium). Afterwards, the cells were washed three times with AIM-V medium, the cell number and viability was checked and the cell number adjusted to 0.3 Mio/ml.

Meanwhile, PBMC as effector cells were prepared by density gradient centrifugation (Histopaque-1077, Sigma #H8889) according to the manufacturer's protocol (washing steps 1× at 400 g and 2× at 350 g 10 min each). The cell number and viability was checked and the cell number adjusted to 15 Mio/ml.

100 µl calcein-stained target cells were plated in round-bottom 96-well plates, 50 µl diluted antibody was added and 50 µl effector cells. In some experiments the target cells were mixed with Redimune® NF Liquid (ZLB Behring) at a concentration of 10 mg/ml Redimune.

As controls served the spontaneous lysis, determined by co-culturing target and effector cells without antibody and the maximal lysis, determined by 1% Triton X-100 lysis of target cells only. The plate was incubated for 4 hours at 37° C. in a humidified cell incubator.

The killing of target cells was assessed by measuring LDH release from damaged cells using the Cytotoxicity Detection kit (LDH Detection Kit, Roche #1 644 793) according to the manufacturer's instruction. Briefly, 100 µl supernatant from each well was mixed with 100 µl substrate from the kit in a transparent flat bottom 96 well plate. The Vmax values of the substrate's colour reaction was determined in an ELISA reader at 490 nm for at least 10 min. Percentage of specific antibody-mediated killing was calculated as follows: ((A−SR)/(MR−SR)×100, where A is the mean of Vmax at a specific antibody concentration, SR is the mean of Vmax of the spontaneous release and MR is the mean of Vmax of the maximal release.

As additional readout the calcein retention of intact target cells was assessed by lysing the remaining target cells in borate buffer (5 mM sodium borate+0.1% Triton) and measuring the calcein fluorescence in a fluorescence plate reader.

FIG. 4 shows the in vitro ADCC of glycoengineered (GE) humanized CUB4 Antibody No. 69 GE with an amount of fucose of 65% or less compared with the ADCC of the chimeric glycoengineered (GE) CUB4 and wildtype (wt=non glycoengineered chimeric CUB4 Antibody and negative human IgG control.

EXAMPLE 5

Stimulation of CDCP1 Phosphorylation in DU-145 Cells $2 \times 10^5$ per 6 well Du-145 cells cultured in DMEM (Paa cat. No. E15-0011) 2 mM L-glutamine (Sigma Cat. No. G7513, 2 mM sodium pyrovate, 10% FCS (PAA Cat. No E15-0011) over night. Cells were incubated with 20 µg/ml of the different humanized CUB4 antibodies for 10 min. Cess were lysed with freshly prepared ice cooled RIPA lyses buffer. (RIPA—Puffer 1% NP40, 1% DOC, 0.1% SDS, 150 mM NaCl, 10 mM Tris/HCl, pH 7.4, 1 mM PMSF in Ethanol, 10 µg/mL Aprotinin, 0.4 mM Orthovanadat). After 10 min on ice cell lysates were centrifuged for 10 min at 10000 rpm. The lysates were separated on SDS-PAGe by standard protocol and transferred to nitrocellulose by Western blotting. Western Blots were detected by an anti-phosphotyrosine antibody (4G10) or an anti-phosphoCDCP1 antibody. The intensity of the phosphorylated CDCP1 was determined by densiometric scanning (Biorad GS 800 densiometer).

TABLE 4

Percentage (%) stimulation of humanized CUB4 antibodies (relative to chimeric CUB4)

| Humanized CUB4 Antibody No. | Percent (%) stimulation |
| --- | --- |
| Chimeric CUB4 | 100% |
| 80 | 133% |
| 69 | 112 |
| 47 | 96 |
| 135 | 72 |

All Humanized CUB4 Antibodies No. 80, No. 69, 47 and 135 showed a stimulation of CDCP1 phosphorylation in DU-145 cells.

EXAMPLE 6

In Vivo Tumor Inhibition of Humanized CUB4 Antibodies

A) Study name: CDCP1_PZ_H322M_007

The present in vivo study was performed to compare the efficacy of chimeric anti-CDCP1 antibody CUB4 with humanized versions of CUB4 antibody in the NCI-H322M non small cell lung cancer model.

H322M non small cell lung cancer cells were obtained from the NCI collection. Tumor cell line was routinely cultured in RPMI 1640 medium supplemented with 10% fetal bovine serum and 2 mM L-glutamine at 37° C. in a water-saturated atmosphere at 5% CO2. Passage 4 was used for cell transplantation.

The human non small cell lung cancer cell line H322M was subcutaneously inoculated ($5 \times 10^6$ cells) with matrigel into the right flank of the mice.

Animal treatment started at the day of randomisation, 19 days after cell transplantation. Antibodies were administered i.p. q7d on study day 19, 26, 33, 40, and 47 at the indicated dosage of 25 mg/kg. Also the corresponding vehicle was administered on the same days. The administration volume was 10 ml/kg.

Humanized CUB4 Antibody No. 69 is based on VH and VL of SEQ ID NO:3 and SEQ ID NO:15.

Humanized CUB4 Antibody No. 135 is based on VH and VL of SEQ ID NO:3 and SEQ ID NO:23.

Figure 5A:
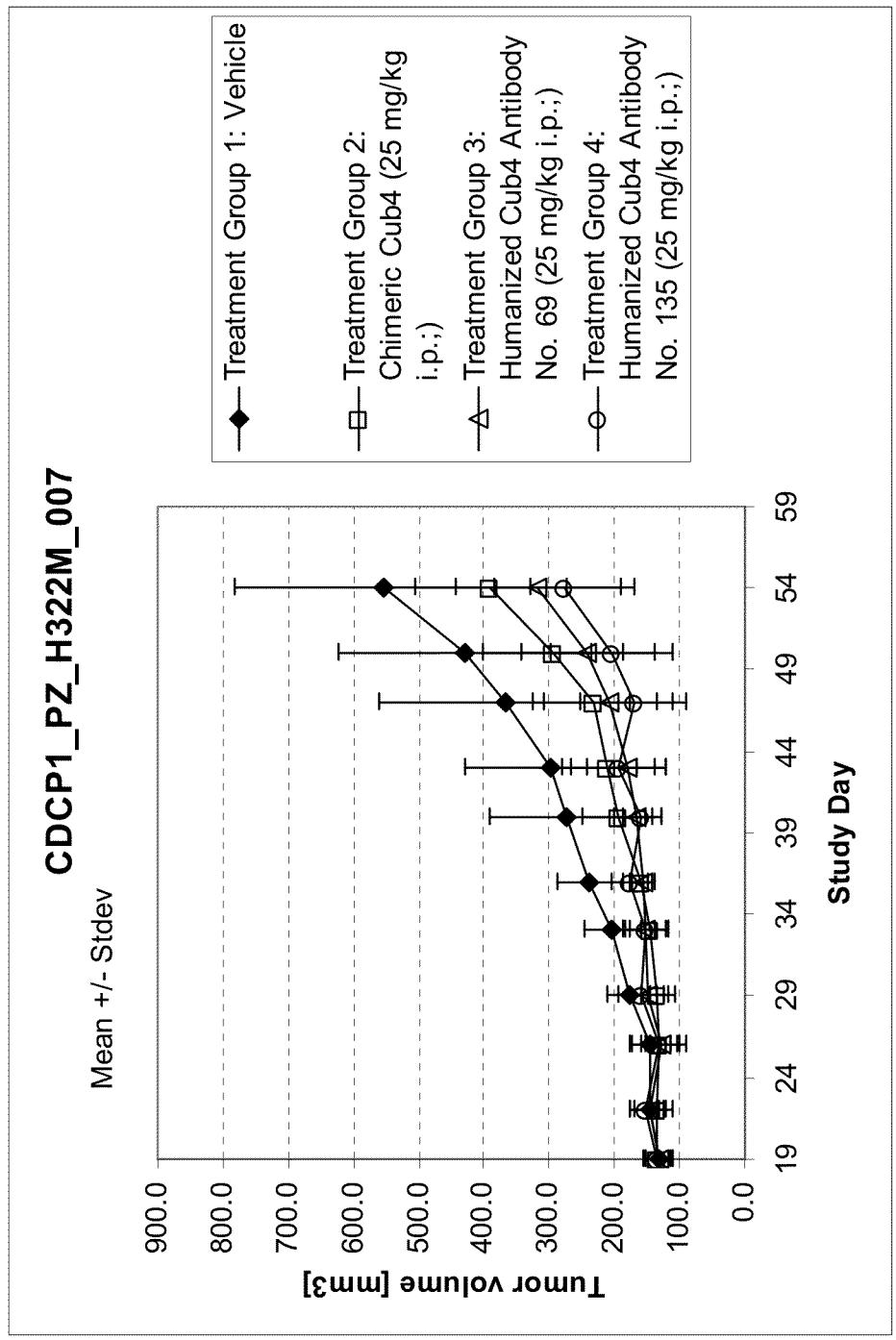

Groups:
Treatment Group 1: Vehicle
Treatment Group 2: Chimeric CUB4 (25 mg/kg i.p.);
Treatment Group 3: Humanized CUB4 Antibody No. 69 (25 mg/kg i.p.);
Treatment Group 4: Humanized CUB4 Antibody No. 135 (25 mg/kg i.p.);

In FIG. 5a the in vivo tumor growth inhibition in human lung cancer H322M xenograft of humanized CUB4 Antibodies No. 69 and No. 135 and chimeric CUB4 antibody shown with a clearly improved in vivo tumor growth inhibition of both humanized CUB4 Antibodies No. 69 and No. 135 compared to chimeric CUB4 antibody.

B) Study name: CDCP1_PZ_H322M_004

The present in vivo study was performed to compare the efficacy of murine anti-CDCP1 antibody CUB4 with chimeric anti-CDCP1 antibody CUB4 (mouse VH and VL with human IgG1 constant region) in the NCI-H322M non small cell lung cancer model.

H322M non small cell lung cancer cells were obtained from the NCI collection. Tumor cell line was routinely cultured in RPMI 1640 medium supplemented with 10% fetal bovine serum and 2 mM L-glutamine at 37° C. in a water-saturated atmosphere at 5% CO2. Passage 4 was used for cell transplantation.

The human non small cell lung cancer cell line H322M was subcutaneously inoculated ($5 \times 10^6$ cells) with matrigel into the right flank of the mice.

Animal treatment started at the day of randomisation 17 days after cell transplantation. Antibodies were administered i.p. q7d until study termination day 59 at the indicated dosage of 10 mg/kg. Also the corresponding vehicle was administered on the same days. The administration volume was 10 ml/kg.

Groups:
Treatment Group 1: Vehicle
Treatment Group 4: Murine CUB4 (10 mg/kg i.p.)
Treatment Group 5: Chimeric CUB4 (10 mg/kg i.p.)

In FIG. 5b the in vivo tumor growth inhibition in human lung cancer H322M xenograft of mouse CUB4 antibody and chimeric CUB4 antibody is shown with an improved in vivo tumor growth inhibition of chimeric CUB4 antibody compared to mouse CUB4 antibody.

What is claimed is:

1. A method for treating a patient suffering from a CDCP1 expressing cancer, said method comprising administering to a patient diagnosed as having such a disease an effective amount of a pharmaceutical composition comprising an antibody which specifically binds to human CDCP1 comprising:
(a) a variable heavy chain domain (VH) of SEQ ID NO:3, or
(b) a variable light chain domain (VL) of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

2. The method of claim 1, wherein said CDCP1 expressing cancer is a breast cancer, an ovarian cancer, a cervical cancer, a lung cancer or a prostate cancer.

* * * * *

SEQUENCE LISTING

<160> NUMBER OF SEQ ID NOS: 32

<210> SEQ ID NO 1
<211> LENGTH: 120
<212> TYPE: PRT
<213> ORGANISM: Mus musculus

<400> SEQUENCE: 1

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Pro Asp Tyr Asp Gly Val Trp Phe Ala Tyr Trp Gly Gln
            100                 105                 110

Gly Thr Leu Val Thr Val Ser Ala
        115                 120
```

<210> SEQ ID NO 2
<211> LENGTH: 106
<212> TYPE: PRT
<213> ORGANISM: Mus musculus

<400> SEQUENCE: 2

```
Gln Ile Val Leu Thr Gln Ser Pro Ala Ile Met Ser Ala Ser Pro Gly
1               5                   10                  15

Glu Lys Val Thr Met Thr Cys Ser Val Ser Ser Ser Val Phe Tyr Val
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Gly Gly Thr Lys Leu Glu Ile Lys
            100                 105
```

<210> SEQ ID NO 3
<211> LENGTH: 120
<212> TYPE: PRT
<213> ORGANISM: Artificial
<220> FEATURE:
<223> OTHER INFORMATION: hHC4-H - humanized VH of CUB4

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30
```

```
Gly Met Ser Trp Val Arg Gln Ala Pro Gly Lys Gly Leu Glu Trp Val
         35                  40                  45

Ala Thr Ile Ser Ser Gly Gly Ser Tyr Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Pro Asp Tyr Asp Gly Val Trp Phe Ala Tyr Trp Gly Gln
            100                 105                 110

Gly Thr Leu Val Thr Val Ser Ser
            115                 120

<210> SEQ ID NO 4
<211> LENGTH: 120
<212> TYPE: PRT
<213> ORGANISM: Artificial
<220> FEATURE:
<223> OTHER INFORMATION: hHC4-c - humanized VH of CUB4

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Ser Tyr
             20                  25                  30

Gly Met Ser Trp Val Arg Gln Ala Pro Gly Lys Gly Leu Glu Trp Val
         35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Pro Asp Tyr Asp Gly Val Trp Phe Ala Tyr Trp Gly Gln
            100                 105                 110

Gly Thr Leu Val Thr Val Ser Ser
            115                 120

<210> SEQ ID NO 5
<211> LENGTH: 120
<212> TYPE: PRT
<213> ORGANISM: Artificial
<220> FEATURE:
<223> OTHER INFORMATION: hHC4-a - humanized VH of CUB4

<400> SEQUENCE: 5

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Asn Ser Tyr
             20                  25                  30

Gly Met Ser Trp Val Arg Gln Ala Pro Gly Lys Gly Leu Glu Trp Val
         35                  40                  45

Ser Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95
```

```
Ala Arg His Pro Asp Tyr Asp Gly Val Trp Phe Ala Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial
<220> FEATURE:
<223> OTHER INFORMATION: hHC4-d - humanized VH of CUB4

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Asp Tyr Asp Gly Val Trp Phe Ala Tyr Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial
<220> FEATURE:
<223> OTHER INFORMATION: hHC4-04 - humanized VH of CUB4

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Asp Tyr Asp Gly Val Trp Phe Ala Tyr Trp Gly Gln
            100                 105                 110

Gly Thr Leu Val Thr Val Ser Ser
        115                 120

<210> SEQ ID NO 8
<211> LENGTH: 120
<212> TYPE: PRT
```

-continued

```
<213> ORGANISM: Artificial
<220> FEATURE:
<223> OTHER INFORMATION: hHC4-K - humanized VH of CUB4

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ser Ser Ile Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Asp Tyr Asp Gly Val Trp Phe Ala Tyr Trp Gly Gln
            100                 105                 110

Gly Thr Leu Val Thr Val Ser Ser
        115                 120

<210> SEQ ID NO 9
<211> LENGTH: 120
<212> TYPE: PRT
<213> ORGANISM: Artificial
<220> FEATURE:
<223> OTHER INFORMATION: hHC4-K2 - humanized VH of CUB4

<400> SEQUENCE: 9

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ser Ser Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Asp Tyr Asp Gly Val Trp Phe Ala Tyr Trp Gly Gln
            100                 105                 110

Gly Thr Leu Val Thr Val Ser Ser
        115                 120

<210> SEQ ID NO 10
<211> LENGTH: 120
<212> TYPE: PRT
<213> ORGANISM: Artificial
<220> FEATURE:
<223> OTHER INFORMATION: hHC4-I - humanized VH of CUB4

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30
```

```
Ala Met Ser Trp Val Arg Gln Ala Pro Gly Lys Gly Leu Glu Trp Val
        35                  40                  45

Ser Ala Ile Ser Ser Gly Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Pro Asp Tyr Asp Gly Val Trp Phe Ala Tyr Trp Gly Gln
            100                 105                 110

Gly Thr Leu Val Thr Val Ser Ser
            115                 120

<210> SEQ ID NO 11
<211> LENGTH: 120
<212> TYPE: PRT
<213> ORGANISM: Artificial
<220> FEATURE:
<223> OTHER INFORMATION: hHC4-07 - humanized VH of CUB4

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Pro Asp Tyr Asp Gly Val Trp Phe Ala Tyr Trp Gly Gln
            100                 105                 110

Gly Thr Leu Val Thr Val Ser Ser
            115                 120

<210> SEQ ID NO 12
<211> LENGTH: 120
<212> TYPE: PRT
<213> ORGANISM: Artificial
<220> FEATURE:
<223> OTHER INFORMATION: hHC4-03 - humanized VH of CUB4

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ser Ala Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Lys His Pro Asp Tyr Asp Gly Val Trp Phe Ala Tyr Trp Gly Gln
                100                 105                 110

Gly Thr Leu Val Thr Val Ser Ser
        115                 120

<210> SEQ ID NO 13
<211> LENGTH: 120
<212> TYPE: PRT
<213> ORGANISM: Artificial
<220> FEATURE:
<223> OTHER INFORMATION: hHC4-b - humanized VH of CUB4

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ser Tyr
            20                  25                  30

Ser Met Asn Trp Val Arg Gln Ala Pro Gly Lys Gly Leu Glu Trp Val
        35                  40                  45

Ser Ser Ile Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Asp Tyr Asp Gly Val Trp Phe Ala Tyr Trp Gly Gln
                100                 105                 110

Gly Thr Leu Val Thr Val Ser Ser
        115                 120

<210> SEQ ID NO 14
<211> LENGTH: 106
<212> TYPE: PRT
<213> ORGANISM: Artificial
<220> FEATURE:
<223> OTHER INFORMATION: hLC4-M - humanized VL of CUB4

<400> SEQUENCE: 14

Glu Ile Val Leu Thr Gln Ser Pro Ala Thr Leu Ser Leu Ser Pro Gly
1               5                   10                  15

Glu Arg Ala Thr Met Ser Cys Gly Ala Ser Ser Ser Val Phe Tyr Leu
            20                  25                  30

His Trp Tyr Gln Gln Lys Pro Gly Leu Ala Pro Arg Leu Trp Ile Tyr
        35                  40                  45

Asp Thr Ser Lys Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Asn Ser Asn Pro Pro Thr
                85                  90                  95

Phe Gly Gly Gly Thr Lys Val Glu Ile Lys
                100                 105

<210> SEQ ID NO 15
<211> LENGTH: 106
<212> TYPE: PRT
<213> ORGANISM: Artificial
<220> FEATURE:
```

<223> OTHER INFORMATION: hLC4-L2 - humanized VL of CUB4

<400> SEQUENCE: 15

```
Glu Ile Val Leu Thr Gln Ser Pro Ala Thr Leu Ser Leu Ser Pro Gly
1               5                   10                  15
Glu Arg Ala Thr Met Ser Cys Ser Val Ser Ser Val Phe Tyr Leu
            20                  25                  30
His Trp Tyr Gln Gln Lys Pro Gly Gln Ala Pro Arg Leu Trp Ile Tyr
                35                  40                  45
Asp Thr Ser Lys Leu Ala Ser Gly Ile Pro Ala Arg Phe Ser Gly Ser
        50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys Gln Gln Trp Asn Ser Asn Pro Pro Thr
                85                  90                  95
Phe Gly Gly Gly Thr Lys Val Glu Ile Lys
            100                 105
```

<210> SEQ ID NO 16
<211> LENGTH: 106
<212> TYPE: PRT
<213> ORGANISM: Artificial
<220> FEATURE:
<223> OTHER INFORMATION: hLC4-K - humanized VL of CUB4

<400> SEQUENCE: 16

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Ser Val Phe Tyr Leu
            20                  25                  30
His Trp Tyr Gln Gln Lys Pro Gly Gln Ala Pro Arg Leu Trp Ile Tyr
                35                  40                  45
Asp Thr Ser Lys Leu Ala Ser Gly Ile Pro Ala Arg Phe Ser Gly Ser
        50                  55                  60
Gly Ser Gly Thr Asp Phe Thr Leu Thr Ile Ser Ser Leu Glu Pro Glu
65                  70                  75                  80
Asp Phe Ala Val Tyr Tyr Cys Gln Gln Trp Asn Ser Asn Pro Pro Thr
                85                  90                  95
Phe Gly Gly Gly Thr Lys Val Glu Ile Lys
            100                 105
```

<210> SEQ ID NO 17
<211> LENGTH: 106
<212> TYPE: PRT
<213> ORGANISM: Artificial
<220> FEATURE:
<223> OTHER INFORMATION: hLC4-L - humanized VL of CUB4

<400> SEQUENCE: 17

```
Glu Ile Val Leu Thr Gln Ser Pro Ala Thr Leu Ser Leu Ser Pro Gly
1               5                   10                  15
Glu Arg Ala Thr Met Ser Cys Arg Ala Ser Ser Val Phe Tyr Leu
            20                  25                  30
His Trp Tyr Gln Gln Lys Pro Gly Gln Ala Pro Arg Leu Trp Ile Tyr
                35                  40                  45
Asp Thr Ser Lys Leu Ala Ser Gly Ile Pro Ala Arg Phe Ser Gly Ser
        50                  55                  60
Gly Ser Gly Thr Asp Phe Thr Leu Thr Ile Ser Ser Leu Glu Pro Glu
```

```
                65                  70                  75                  80
Asp Phe Ala Val Tyr Tyr Cys Gln Gln Trp Asn Ser Asn Pro Pro Thr
                    85                  90                  95

Phe Gly Gly Gly Thr Lys Val Glu Ile Lys
                100                 105

<210> SEQ ID NO 18
<211> LENGTH: 106
<212> TYPE: PRT
<213> ORGANISM: Artificial
<220> FEATURE:
<223> OTHER INFORMATION: hLC4-J - humanized VL of CUB4

<400> SEQUENCE: 18

Glu Ile Val Met Thr Gln Ser Pro Ala Thr Leu Ser Leu Ser Pro Gly
1               5                   10                  15

Glu Arg Ala Thr Met Ser Cys Arg Ala Ser Ser Ser Val Phe Tyr Leu
                20                  25                  30

His Trp Tyr Gln Gln Lys Pro Gly Gln Ala Pro Arg Leu Trp Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Val Tyr Tyr Cys Gln Gln Trp Asn Ser Asn Pro Pro Thr
                    85                  90                  95

Phe Gly Gly Gly Thr Lys Val Glu Ile Lys
                100                 105

<210> SEQ ID NO 19
<211> LENGTH: 106
<212> TYPE: PRT
<213> ORGANISM: Artificial
<220> FEATURE:
<223> OTHER INFORMATION: hLC4-b - humanized VL of CUB4

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Val Ser Ser Ser Val Phe Tyr Val
                20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Asn Ser Asn Pro Pro Thr
                    85                  90                  95

Phe Gly Gly Gly Thr Lys Val Glu Ile Lys
                100                 105

<210> SEQ ID NO 20
<211> LENGTH: 106
<212> TYPE: PRT
<213> ORGANISM: Artificial
<220> FEATURE:
<223> OTHER INFORMATION: hLC4-c - humanized VL of CUB4

<400> SEQUENCE: 20
```

```
Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Val Phe Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Trp Asn Ser Asn Pro Pro Thr
                85                  90                  95

Phe Gly Gly Gly Thr Lys Val Glu Ile Lys
            100                 105
```

<210> SEQ ID NO 21
<211> LENGTH: 106
<212> TYPE: PRT
<213> ORGANISM: Artificial
<220> FEATURE:
<223> OTHER INFORMATION: hLC4-a - humanized VL of CUB4

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Ser Val Ser Ser Ser Val Phe Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Asn Ser Asn Pro Pro Thr
                85                  90                  95

Phe Gly Gly Gly Thr Lys Val Glu Ile Lys
            100                 105
```

<210> SEQ ID NO 22
<211> LENGTH: 106
<212> TYPE: PRT
<213> ORGANISM: Artificial
<220> FEATURE:
<223> OTHER INFORMATION: hLC4-d - humanized VL of CUB4

<400> SEQUENCE: 22

```
Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Val Phe Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Glu Tyr Thr Leu Thr Ile Ser Ser Leu Gln Ser Glu
65                  70                  75                  80

Asp Phe Ala Val Tyr Tyr Cys Gln Gln Trp Asn Ser Asn Pro Pro Thr
```

Phe Gly Gly Gly Thr Lys Val Glu Ile Lys
            100              105

<210> SEQ ID NO 23
<211> LENGTH: 106
<212> TYPE: PRT
<213> ORGANISM: Artificial
<220> FEATURE:
<223> OTHER INFORMATION: hLC4-e - humanized VL of CUB4

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Phe Tyr Val
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Asn Ser Asn Pro Pro Thr
                85                  90                  95

Phe Gly Gly Gly Thr Lys Val Glu Ile Lys
            100              105

<210> SEQ ID NO 24
<211> LENGTH: 106
<212> TYPE: PRT
<213> ORGANISM: Artificial
<220> FEATURE:
<223> OTHER INFORMATION: hLC4-f - humanized VL of CUB4

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Phe Tyr Val
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Asn Ser Asn Pro Pro Thr
                85                  90                  95

Phe Gly Gly Gly Thr Lys Val Glu Ile Lys
            100              105

<210> SEQ ID NO 25
<211> LENGTH: 106
<212> TYPE: PRT
<213> ORGANISM: Artificial
<220> FEATURE:
<223> OTHER INFORMATION: hLC4-I - humanized VL of CUB4

<400> SEQUENCE: 25

Glu Ile Val Met Thr Gln Ser Pro Ala Thr Leu Ser Leu Ser Pro Gly
1               5                   10                  15

Glu Arg Ala Thr Leu Ser Cys Arg Ala Ser Ser Val Phe Tyr Leu
            20                  25                  30

Ser Trp Tyr Gln Gln Lys Pro Gly Gln Ala Pro Arg Leu Trp Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Val Tyr Tyr Cys Gln Gln Trp Asn Ser Asn Pro Pro Thr
                85                  90                  95

Phe Gly Gly Gly Thr Lys Val Glu Ile Lys
            100                 105

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe

```
                275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 27
<211> LENGTH: 107
<212> TYPE: PRT
<213> ORGANISM: Homo sapiens

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 104
<212> TYPE: PRT
<213> ORGANISM: Homo sapiens

<400> SEQUENCE: 28

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 29
<211> LENGTH: 836
<212> TYPE: PRT
<213> ORGANISM: Homo sapiens

<400> SEQUENCE: 29

Met Ala Gly Leu Asn Cys Gly Val Ser Ile Ala Leu Leu Gly Val Leu
1               5                   10                  15
```

-continued

```
Leu Leu Gly Ala Ala Arg Leu Pro Arg Gly Ala Glu Ala Phe Glu Ile
         20                  25                  30
Ala Leu Pro Arg Glu Ser Asn Ile Thr Val Leu Ile Lys Leu Gly Thr
         35                  40                  45
Pro Thr Leu Leu Ala Lys Pro Cys Tyr Ile Val Ile Ser Lys Arg His
 50                  55                  60
Ile Thr Met Leu Ser Ile Lys Ser Gly Glu Arg Ile Val Phe Thr Phe
 65                  70                  75                  80
Ser Cys Gln Ser Pro Glu Asn His Phe Val Ile Glu Ile Gln Lys Asn
                 85                  90                  95
Ile Asp Cys Met Ser Gly Pro Cys Pro Phe Gly Glu Val Gln Leu Gln
             100                 105                 110
Pro Ser Thr Ser Leu Leu Pro Thr Leu Asn Arg Thr Phe Ile Trp Asp
         115                 120                 125
Val Lys Ala His Lys Ser Ile Gly Leu Glu Leu Gln Phe Ser Ile Pro
130                 135                 140
Arg Leu Arg Gln Ile Gly Pro Gly Glu Ser Cys Pro Asp Gly Val Thr
145                 150                 155                 160
His Ser Ile Ser Gly Arg Ile Asp Ala Thr Val Val Arg Ile Gly Thr
                 165                 170                 175
Phe Cys Ser Asn Gly Thr Val Ser Arg Ile Lys Met Gln Glu Gly Val
             180                 185                 190
Lys Met Ala Leu His Leu Pro Trp Phe His Pro Arg Asn Val Ser Gly
         195                 200                 205
Phe Ser Ile Ala Asn Arg Ser Ser Ile Lys Arg Leu Cys Ile Ile Glu
210                 215                 220
Ser Val Phe Glu Gly Glu Gly Ser Ala Thr Leu Met Ser Ala Asn Tyr
225                 230                 235                 240
Pro Glu Gly Phe Pro Glu Asp Glu Leu Met Thr Trp Gln Phe Val Val
                 245                 250                 255
Pro Ala His Leu Arg Ala Ser Val Ser Phe Leu Asn Phe Asn Leu Ser
             260                 265                 270
Asn Cys Glu Arg Lys Glu Arg Val Glu Tyr Tyr Ile Pro Gly Ser
         275                 280                 285
Thr Thr Asn Pro Glu Val Phe Lys Leu Glu Asp Lys Gln Pro Gly Asn
290                 295                 300
Met Ala Gly Asn Phe Asn Leu Ser Leu Gln Gly Cys Asp Gln Asp Ala
305                 310                 315                 320
Gln Ser Pro Gly Ile Leu Arg Leu Gln Phe Gln Val Leu Val Gln His
                 325                 330                 335
Pro Gln Asn Glu Ser Asn Lys Ile Tyr Val Val Asp Leu Ser Asn Glu
             340                 345                 350
Arg Ala Met Ser Leu Thr Ile Glu Pro Arg Pro Val Lys Gln Ser Arg
         355                 360                 365
Lys Phe Val Pro Gly Cys Phe Val Cys Leu Glu Ser Arg Thr Cys Ser
370                 375                 380
Ser Asn Leu Thr Leu Thr Ser Gly Ser Lys His Lys Ile Ser Phe Leu
385                 390                 395                 400
Cys Asp Asp Leu Thr Arg Leu Trp Met Asn Val Glu Lys Thr Ile Ser
                 405                 410                 415
Cys Thr Asp His Arg Tyr Cys Gln Arg Lys Ser Tyr Ser Leu Gln Val
             420                 425                 430
```

-continued

```
Pro Ser Asp Ile Leu His Leu Pro Val Glu Leu His Asp Phe Ser Trp
        435                 440                 445

Lys Leu Leu Val Pro Lys Asp Arg Leu Ser Leu Val Leu Val Pro Ala
450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
                485                 490                 495

Ser Phe Cys Pro Gly Gly Ser Ile Lys Gln Ile Gln Val Lys Gln Asn
            500                 505                 510

Ile Ser Val Thr Leu Arg Thr Phe Ala Pro Ser Phe Arg Gln Glu Ala
        515                 520                 525

Ser Arg Gln Gly Leu Thr Val Ser Phe Ile Pro Tyr Phe Lys Glu Glu
530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
                565                 570                 575

Asn Ile Ser Val Pro Arg Asp Gln Val Ala Cys Leu Thr Phe Phe Lys
            580                 585                 590

Glu Arg Ser Gly Val Val Cys Gln Thr Gly Arg Ala Phe Met Ile Ile
        595                 600                 605

Gln Glu Gln Arg Thr Arg Ala Glu Glu Ile Phe Ser Leu Asp Glu Asp
610                 615                 620

Val Leu Pro Lys Pro Ser Phe His His His Ser Phe Trp Val Asn Ile
625                 630                 635                 640

Ser Asn Cys Ser Pro Thr Ser Gly Lys Gln Leu Asp Leu Leu Phe Ser
                645                 650                 655

Val Thr Leu Thr Pro Arg Thr Val Asp Leu Thr Val Ile Leu Ile Ala
            660                 665                 670

Ala Val Gly Gly Gly Val Leu Leu Leu Ser Ala Leu Gly Leu Ile Ile
        675                 680                 685

Cys Cys Val Lys Lys Lys Lys Lys Thr Asn Lys Gly Pro Ala Val
690                 695                 700

Gly Ile Tyr Asn Gly Asn Ile Asn Thr Glu Met Pro Arg Gln Pro Lys
705                 710                 715                 720

Lys Phe Gln Lys Gly Arg Lys Asp Asn Asp Ser His Val Tyr Ala Val
                725                 730                 735

Ile Glu Asp Thr Met Val Tyr Gly His Leu Leu Gln Asp Ser Ser Gly
            740                 745                 750

Ser Phe Leu Gln Pro Glu Val Asp Thr Tyr Arg Pro Phe Gln Gly Thr
        755                 760                 765

Met Gly Val Cys Pro Pro Ser Pro Thr Ile Cys Ser Arg Ala Pro
770                 775                 780

Thr Ala Lys Leu Ala Thr Glu Glu Pro Pro Arg Ser Pro Pro Glu
785                 790                 795                 800

Ser Glu Ser Glu Pro Tyr Thr Phe Ser His Pro Asn Asn Gly Asp Val
                805                 810                 815

Ser Ser Lys Asp Thr Asp Ile Pro Leu Leu Asn Thr Gln Glu Pro Met
            820                 825                 830

Glu Pro Ala Glu
        835
```

<210> SEQ ID NO 30
<211> LENGTH: 663
<212> TYPE: PRT
<213> ORGANISM: Homo sapiens

<400> SEQUENCE: 30

```
Met Ala Gly Leu Asn Cys Gly Val Ser Ile Ala Leu Leu Gly Val Leu
1               5                   10                  15

Leu Leu Gly Ala Ala Arg Leu Pro Arg Gly Ala Glu Ala Phe Glu Ile
            20                  25                  30

Ala Leu Pro Arg Glu Ser Asn Ile Thr Val Leu Ile Lys Leu Gly Thr
        35                  40                  45

Pro Thr Leu Leu Ala Lys Pro Cys Tyr Ile Val Ile Ser Lys Arg His
    50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190

Lys Met Ala Leu His Leu Pro Trp Phe His Pro Arg Asn Val Ser Gly
        195                 200                 205

Phe Ser Ile Ala Asn Arg Ser Ser Ile Lys Arg Leu Cys Ile Ile Glu
    210                 215                 220

Ser Val Phe Glu Gly Glu Gly Ser Ala Thr Leu Met Ser Ala Asn Tyr
225                 230                 235                 240

Pro Glu Gly Phe Pro Glu Asp Glu Leu Met Thr Trp Gln Phe Val Val
                245                 250                 255

Pro Ala His Leu Arg Ala Ser Val Ser Phe Leu Asn Phe Asn Leu Ser
            260                 265                 270

Asn Cys Glu Arg Lys Glu Glu Arg Val Glu Tyr Tyr Ile Pro Gly Ser
        275                 280                 285

Thr Thr Asn Pro Glu Val Phe Lys Leu Glu Asp Lys Gln Pro Gly Asn
    290                 295                 300

Met Ala Gly Asn Phe Asn Leu Ser Leu Gln Gly Cys Asp Gln Asp Ala
305                 310                 315                 320

Gln Ser Pro Gly Ile Leu Arg Leu Gln Phe Gln Val Leu Val Gln His
                325                 330                 335

Pro Gln Asn Glu Ser Asn Lys Ile Tyr Val Val Asp Leu Ser Asn Glu
            340                 345                 350

Arg Ala Met Ser Leu Thr Ile Glu Pro Arg Pro Val Lys Gln Ser Arg
        355                 360                 365

Lys Phe Val Pro Gly Cys Phe Val Cys Leu Glu Ser Arg Thr Cys Ser
    370                 375                 380
```

```
Ser Asn Leu Thr Leu Thr Ser Gly Ser Lys His Lys Ile Ser Phe Leu
385                 390                 395                 400

Cys Asp Asp Leu Thr Arg Leu Trp Met Asn Val Glu Lys Thr Ile Ser
            405                 410                 415

Cys Thr Asp His Arg Tyr Cys Gln Arg Lys Ser Tyr Ser Leu Gln Val
        420                 425                 430

Pro Ser Asp Ile Leu His Leu Pro Val Glu Leu His Asp Phe Ser Trp
    435                 440                 445

Lys Leu Leu Val Pro Lys Asp Arg Leu Ser Leu Val Leu Val Pro Ala
450                 455                 460

Gln Lys Leu Gln Gln His Thr His Glu Lys Pro Cys Asn Thr Ser Phe
465                 470                 475                 480

Ser Tyr Leu Val Ala Ser Ala Ile Pro Ser Gln Asp Leu Tyr Phe Gly
            485                 490                 495

Ser Phe Cys Pro Gly Gly Ser Ile Lys Gln Ile Gln Val Lys Gln Asn
        500                 505                 510

Ile Ser Val Thr Leu Arg Thr Phe Ala Pro Ser Phe Arg Gln Glu Ala
    515                 520                 525

Ser Arg Gln Gly Leu Thr Val Ser Phe Ile Pro Tyr Phe Lys Glu Glu
530                 535                 540

Gly Val Phe Thr Val Thr Pro Asp Thr Lys Ser Lys Val Tyr Leu Arg
545                 550                 555                 560

Thr Pro Asn Trp Asp Arg Gly Leu Pro Ser Leu Thr Ser Val Ser Trp
            565                 570                 575

Asn Ile Ser Val Pro Arg Asp Gln Val Ala Cys Leu Thr Phe Phe Lys
        580                 585                 590

Glu Arg Ser Gly Val Val Cys Gln Thr Gly Arg Ala Phe Met Ile Ile
    595                 600                 605

Gln Glu Gln Arg Thr Arg Ala Glu Glu Ile Phe Ser Leu Asp Glu Asp
610                 615                 620

Val Leu Pro Lys Pro Ser Phe His His His Ser Phe Trp Val Asn Ile
625                 630                 635                 640

Ser Asn Cys Ser Pro Thr Ser Gly Lys Gln Leu Asp Leu Leu Phe Ser
            645                 650                 655

Val Thr Leu Thr Pro Arg Thr
            660

<210> SEQ ID NO 31
<211> LENGTH: 330
<212> TYPE: PRT
<213> ORGANISM: Homo sapiens

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 327
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
```

```
              130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```